United States Patent [19]
Suzuki

[11] Patent Number: 5,292,316
[45] Date of Patent: Mar. 8, 1994

[54] DISPOSABLE ABSORBENT ARTICLE HAVING MULTI-COMPONENT UPSTANDING LEG GATHERS

[75] Inventor: Migaku Suzuki, Kamakura, Japan

[73] Assignee: Paragon Trade Brands, Inc., Federal Way, Wash.

[21] Appl. No.: 960,902

[22] Filed: Oct. 14, 1992

[51] Int. Cl.⁵ .............................................. A61F 13/15
[52] U.S. Cl. ................................. 604/385.2; 604/358
[58] Field of Search .................. 604/358, 385.1, 385.2

[56] References Cited

U.S. PATENT DOCUMENTS

| | | |
|---|---|---|
| 4,490,148 | 12/1984 | Beckestrom . |
| 4,695,278 | 9/1987 | Lawson . |
| 4,699,620 | 10/1987 | Bernardin ........................ 604/385.2 |
| 4,704,116 | 11/1987 | Enloe . |
| 4,795,454 | 1/1989 | Dragoo . |
| 4,892,528 | 1/1990 | Suzuki . |
| 5,085,654 | 2/1992 | Buell ................................ 604/385.1 |
| 5,246,432 | 9/1993 | Suzuki et al. .................... 604/385.2 |

FOREIGN PATENT DOCUMENTS 4118359  8/1986  Japan .

Primary Examiner—Randall L. Green
Assistant Examiner—Rob Clarke
Attorney, Agent, or Firm—Dressler, Goldsmith, Shore & Milnamow, Ltd.

[57] ABSTRACT

An disposable absorbent article, such as a disposable diaper, includes an absorbent core interposed between a liquid permeable topsheet and a backsheet assembly. The backsheet assembly includes a central liquid impermeable layer and opposite side marginal portions comprising a nonwoven fabric. The liquid impermeable layer includes opposite side edges extending upwardly about respective opposite side edges of the absorbent core to form a pair of standing leg gathers. Each of the standing leg gathers further includes an upper element comprising hydrophobic nonwoven material joined to a respective one of the side edges of the liquid impermeable layer. An elastic means is operatively associated with an upper free edge portion of the respective upper element for elastically contracting each of the standing leg gather.

9 Claims, 2 Drawing Sheets

DISPOSABLE ABSORBENT ARTICLE HAVING MULTI-COMPONENT UPSTANDING LEG GATHERS

TECHNICAL FIELD

The present invention relates generally to a disposable absorbent article, and more particularly to a disposable absorbent article, such as a disposable diaper, having a pair of standing leg gathers which each comprise a liquid impermeable layer and an upper hydrophobic nonwoven material element having an elasticized upper free edge for conforming the article to a wearer.

BACKGROUND OF THE INVENTION

Disposable absorbent articles, such as infant diapers and adult incontinent products have achieved widespread acceptance by consumers. Articles of this nature are typically configured for single use, with an absorbent core or panel of the diaper ordinarily provided in an integrated structure including a liquid permeable topsheet or facing layer, and a liquid impermeable backsheet or backing layer. Adhesive coated tape tabs are typically provided to facilitate convenient fitting of the diaper to the wearer.

Current commercially available absorbent articles typically incorporate a pair of standing leg gathers which extend upwardly generally about respective side edges of the absorbent core. Such a standing leg gather defines a barrier or wall at the respective side edge of a central crotch area of the article, which acts to prevent or retard the lateral flow of fluidic body exudates, such as urine or fluidic fecal material.

U.S. Pat. No. 4,490,148, to Beckestrom, discloses a protector against incontinence comprising an oblong absorbent body which is fixed to a bottom liquid-tight layer, illustrated as a plastic sheet extending outside the absorbent body. The lateral edge portions of the bottom layer are folded in over the absorbent body and form side flaps. The side flaps are fixed at their opposite longitudinal ends to the bottom layer. An elastic element is arranged at an edge of each of the side flaps to elastically contract the side flap. When the protector is put on, the side edges of the side flaps come into elastic sealing contact in the thigh creases of the crotch to provide improved containment of the body exudates.

U.S. Pat. No. 4,892,528, to Suzuki et al., teaches a disposable diaper having an upwardly-extending leakage protecting baffle positioned inwardly of a respective flat elastic leg seal. An inner portion of a hydrophobic and breathable nonwoven fabric element has at its upper free edge elastic means to form the leakage protecting baffle, which extends upwardly about a respective side edge of an absorbent core. An outer portion of the nonwoven fabric element is preferably secured onto a liquid impermeable backsheet to form a leakage protecting seal outwardly of respective side edge of a topsheet.

U.S. Pat. No. 4,695,278, to Lawson, U.S. Pat. No. 4,704,116, to Enloe, and U.S. Pat. No. 4,795,454, to Dragoo, illustrate other variations of standing leg gather constructions.

SUMMARY OF THE INVENTION

An disposable absorbent article embodying the principles of the present invention comprises an absorbent core interposed between a liquid permeable topsheet and a backsheet assembly. The backsheet assembly includes a central liquid impermeable layer and opposite side marginal portions comprising nonwoven fabric. The liquid impermeable layer includes opposite side edges extending upwardly about respective opposite side edges of the absorbent core to form a pair of standing leg gathers. Each of the standing leg gathers further includes an upper element comprising hydrophobic nonwoven material, with each upper element joined to a respective one of the side edges of the liquid impermeable layer. Elastic means are operatively associated with an upper free edge portion of each of the upper elements to elastically contract each of the standing leg gathers.

In certain ones of the illustrated embodiments, the opposite side marginal portions of the backsheet assembly each comprise a separate element joined to the central liquid impermeable layer. Alternatively, the opposite side marginal portions of the backsheet assembly may be formed from a common layer of the nonwoven fabric extending beneath the liquid impermeable layer.

Other features and advantages of the present invention will become readily apparent from the following detailed description, the accompanying drawings, and the appended claims.

BRIEF DESCRIPTION OF THE INVENTION

DETAILED DESCRIPTION

Figure 1:
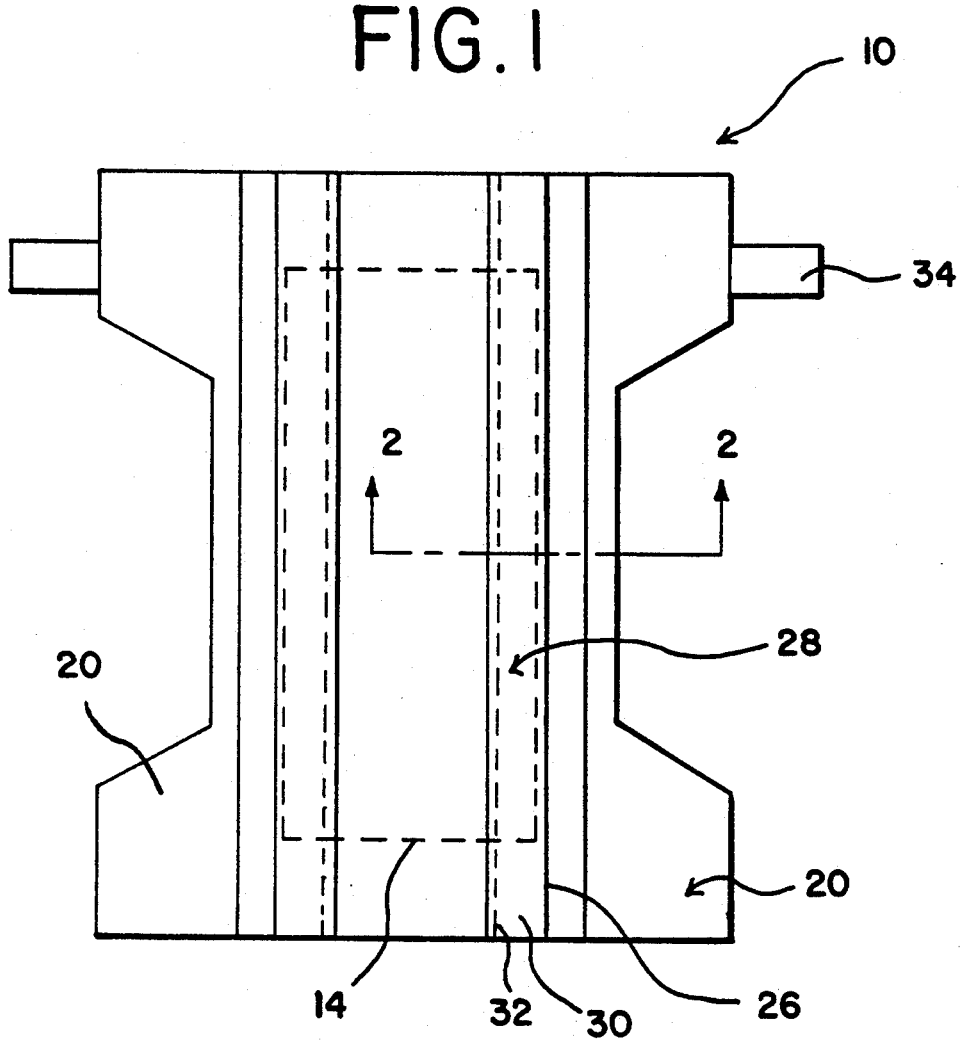
FIG. 1 is a plan view of a disposable absorbent article embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiments illustrated.

Referring now to the drawings, FIG. 1 shows an exemplary disposable absorbent article, such as a disposable diaper, in accordance with the present invention. The disposable absorbent article 10 includes a liquid permeable facing layer or topsheet 12, with the topsheet 12 being adapted for positioning adjacent to a wearer of the article 10. The topsheet 12 is typically made of carded, spunlaced, spunbonded, or thermally-bonded polypropylene or polyester nonwoven fabrics, as is well known in the art.

The article 10 further includes an absorbent core 14, which in the illustrated embodiment, is generally rectangular, but which may be otherwise shaped, such as hourglass-shaped, T-shaped, I-shaped, or otherwise contoured. The absorbent core 14 preferably comprises an absorbent matrix including comminuted wood pulp, sometimes referred to as pulp fluff, and superabsorbent material, which may comprise superabsorbent polymers or the like. Absorbent matrices comprising blends and/or layers of such superabsorbent materials can be employed. If desired, the superabsorbent material may optionally be more heavily concentrated in specifically selected regions of the absorbent core.

Additionally, an absorbent matrix formed in accordance with U.S. Pat. No. 4,573,988, to Pieniak, comprising a compressed absorbent structure including a resilient web of fibers having superabsorbent material incorporated therein, can be used. Subdivided portions of such a compressed absorbent structure can alternately be employed, such as by blending with wood pulp fibers.

The absorbent article 10 further includes a backsheet assembly 16 positioned on the side of the absorbent core 14 that is opposite the topsheet 12. The backsheet assembly 16 includes a central liquid impermeable layer 18 and opposite side marginal portions 20. The central liquid impermeable layer 18 is made of liquid impermeable material as known in the art. Suitable liquid impermeable material may comprise a polymeric film 22 such as polyethylene film. The polymeric film 22 may be combined with a nonwoven fabric to form a composite liquid impermeable layer.

Each of the side marginal portions 20 comprises a nonwoven material, preferably a hydrophobic nonwoven fabric 24 which is liquid resistant and breathable. Such hydrophobic nonwoven material includes spunlaced, spunbonded, meltblown and thermally-bonded nonwoven fabrics comprising polyester, polypropylene or polyethylene fibers. Those fibers may optionally be treated by silicone and the like to be highly hydrophobic.

Figure 2:
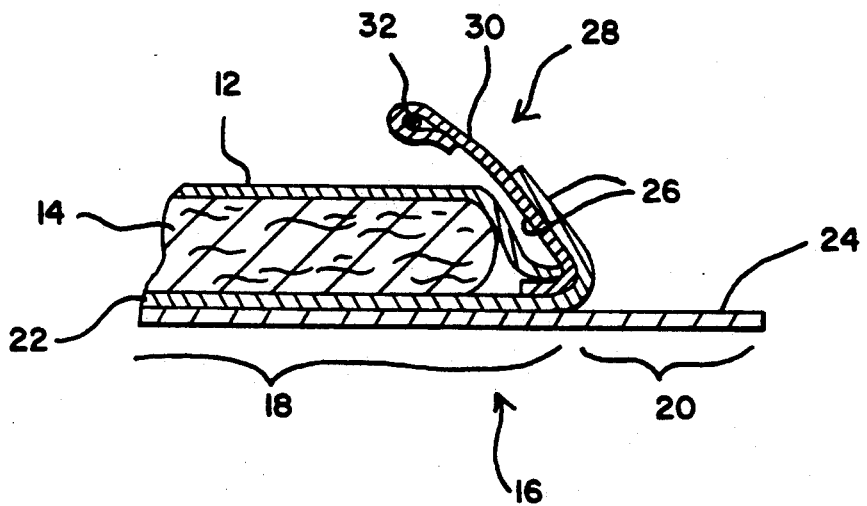
FIG. 2 is a cross-sectional view taken along lines 2—2 of FIG. 1.

In a first particular embodiment, as best seen in FIG. 2, the central liquid impermeable layer 18 comprises a central portion 22 laminated to the hydrophobic nonwoven fabric 24. In this embodiment, a common layer of the nonwoven fabric 24 extends beneath the liquid impermeable film layer, with outward lateral extensions of the nonwoven fabric 24 extending from the central liquid impermeable layer 18 forming the side marginal portions 20 of the backsheet assembly 16.

The liquid impermeable layer 18 includes opposite side edges or extensions 26 extending upwardly generally about respective opposite side edges of the absorbent core 14, as exemplified in FIG. 2, to form a pair of standing leg gathers 28. The pair of standing leg gathers 28 confines the topsheet 12 therebetween to prevent body exudates from wicking through the topsheet 12 to side edges of the article 10.

Each of the pair of standing leg gathers 28 further includes an upper element 30 joined to a respective one of the side edges 26 of the liquid impermeable layer. The upper element 30 preferably comprises hydrophobic nonwoven material which is liquid resistant and breathable, such as a hydrophobic nonwoven fabric. There is provided elastic means 32, comprising one or more elastic elements such as a natural or synthetic monofilament rubber, which is operatively associated with an upper free edge portion of the respective upper element 30 for elastically contracting each of the standing leg gathers 28. The longitudinal ends of each of the standing leg gather 28 are preferably secured inwardly and closed by securement means (not shown) such as heat sealing or adhesive bonding. Such securement means can be arranged to secure each standing gather 28 inwardly to the topsheet 12 generally at the front and rear waist portions of the article.

In the embodiment illustrated in FIG. 2, the upper element 30 of each standing leg gather 28 is substantially coextensive with the respective upturned side edge 26 of the liquid impermeable layer, with a substantial portion of the upper element 30 extending upwardly beyond the respective side edge 26 of the liquid impermeable layer.

It is preferred that the respective side edge 26 of the liquid impermeable layer is arranged to extend upwardly about the side edge of the absorbent core 14 to the extent that the side edge 26 of the liquid impermeable layer is positioned upwardly of a top surface of the absorbent core 14. As a consequence, in an elastically contracted condition, the standing leg gather 28 overlays the top surface of the absorbent core 14, and tends to form a confining structure in an elastically stretched condition of the standing leg gather 28. This configuration provides an effective restraint against the flow of the body exudates.

This construction also permits simple and efficient manufacture. A liquid impermeable polymeric film is positioned on a nonwoven fabric and adhesively or otherwise secured thereto at the central portion 22 to form the backsheet assembly 16. More preferably, thermoplastic polymeric material is extruded onto a nonwoven fabric containing thermoplastic fibers to form a laminate. The laminate is at its center portion pressed, heat-pressed or heat-embossed to form the central portion 22 of the liquid impermeable layer 18. The opposite side edges of the film are left unpressed or unsecured to provide side edges 26 of the liquid impermeable layer and side marginal portions 24 comprising the nonwoven fabric.

A hydrophobic upper nonwoven element 30 including an elastic means 32 at its edge is joined to each of the side edges 26 to form the standing leg gather element 28. The absorbent core 14 is placed on the central liquid impermeable layer 18 and the topsheet 12 is positioned atop the absorbent core 14. Opposite side edges of the topsheet 12 may be each secured to the nonwoven element 30 or to the central liquid impermeable layer 18, followed by inward folding of the standing leg gather element 28 for its end securement.

Alternatively, the hydrophobic upper nonwoven element 30 including the elastic means 32 is first joined to each of side edges of the topsheet 12 to form a facing assembly. After the absorbent core 14 is placed in position on the backsheet assembly 18, the facing assembly is positioned adjacent the absorbent core 14 and each of the upper nonwoven elements 30 thereof is secured to the respective side edge 26 to form the standing leg gather element 28, followed by inwardly folding the standing leg gather elements 28 for end securement.

The absorbent article 10 further includes adhesive tape fasteners 34, as well known in the art, on the rearward portions of the article 10. Each of these fasteners 34 may include a tab-like element having pressure-sensitive adhesive thereon which, when brought into contact with a landing area associated with the forward, outer waist portion of the article 10, secures the article 10 in position.

The absorbent article 10 may also be provided with elasticized waistbands (not shown), as are well-known in the art.

Figure 3:
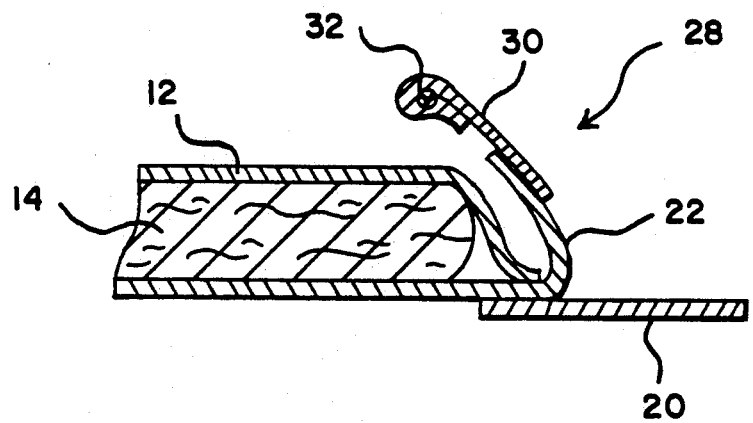
FIG. 3 is a cross-sectional view illustrating an alternate embodiment in accordance with the present invention.

FIG. 3 illustrates another embodiment of the article in accordance with the present invention. The central liquid impermeable layer 18 comprises a polymeric film and includes a central portion 22. A separate nonwoven fabric element is joined to each side margin of the central liquid impermeable layer 18 to form the backsheet assembly 16 including the opposite side marginal portions 20 comprising the nonwoven fabric. The upper nonwoven material element 30 of each standing leg gather 28 is secured at its lower edge to an outer surface of the respective side edge 26 of the liquid impermeable layer.

Figure 4:
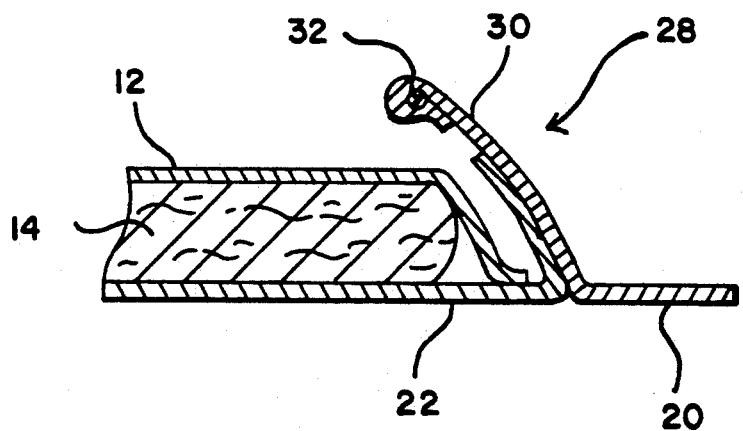
FIG. 4 is a cross-sectional view showing a still another alternate embodiment in accordance with the present invention.

FIG. 4 illustrates another embodiment of the article in accordance with the present invention. The central liquid impermeable layer 18 comprises a polymeric film such as a polyethylene film and includes a central portion 22. A hydrophobic nonwoven fabric is, at its central portion, secured to an outer surface of the respective side edge 26 of the liquid impermeable layer. By this construction, an outer portion of each of the nonwoven fabric elements forms the respective side marginal portion 20 of the backsheet assembly 16. An inner portion of the nonwoven fabric forms the upper element 30 of the standing gather, and includes at its upper free edge an elastic means 32 to elastically contract the standing leg gather 28.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the scope of the claims.

What is claimed is:

1. A disposable absorbent article, comprising:
an absorbent core;
a liquid permeable topsheet positioned on top of said absorbent core to define a top surface;
and a backsheet assembly positioned beneath said absorbent core,
said backsheet assembly including a central liquid impermeable layer, and opposite side marginal portions comprising nonwoven fabric,
said liquid impermeable layer including opposite side edges extending upwardly about respective opposite side edges of said absorbent core to form a pair of standing leg gathers each having an impermeable portion coinciding with the respective side edge of the liquid impermeable layer, each of said leg standing gathers being spaced from said top surface of said topsheet to form a channel between the impermeable portion of each said standing gather and the respective side edge of said absorbent core,
each of said standing leg gathers further including an upper element each comprising hydrophobic nonwoven material, with each said upper element joined to a respective one of said side edges of said impermeable layer, and elastic means operatively associated with an upper free edge portion of the respective upper element for elastically contracting each of the standing leg gathers.

2. A disposable absorbent article in accordance with claim 1, wherein
each said upper element of each standing leg gather is bonded substantially throughout its extent to the respective side edge of the impermeable layer.

3. A disposable absorbent article in accordance with claim 1, wherein
each said upper element of each standing leg gather includes a substantial portion extending upwardly beyond the respective side edge of said impermeable layer.

4. A disposable absorbent article in accordance with claim 1, wherein
said opposite side marginal portions of said backsheet assembly each comprises a separate element joined to said impermeable layer.

5. A disposable absorbent article in accordance with claim 1, wherein
said opposite side marginal portions of said backsheet assembly are formed from a common layer of nonwoven fabric extending beneath said impermeable layer.

6. A disposable absorbent article in accordance with claim 1, wherein
said upper element of each said standing leg gather and the respective said side marginal portion of the backsheet assembly comprise a common hydrophobic nonwoven fabric.

7. A disposable absorbent article, comprising:
an absorbent core;
a liquid permeable topsheet positioned on top of said absorbent core;
and a backsheet assembly positioned beneath said absorbent core,
said backsheet assembly including a central liquid impermeable layer, and opposite side marginal portions comprising nonwoven fabric and each comprising a separate element joined to said impermeable layer,
said liquid impermeable layer including opposite side edges extending upwardly about respective opposite side edges of said absorbent core to form a pair of standing leg gathers,
each of said standing leg gathers further including an upper element each comprising hydrophobic nonwoven material, with each said upper element joined to a respective one of said side edges of said impermeable layer, and elastic means operatively associated with an upper free edge portion of the respective upper element for elastically contracting each of said standing leg gathers.

8. A disposable absorbent article in accordance with claim 7, wherein
said upper element of each said standing leg gather and the respective said side marginal portion of the backsheet assembly comprise a single piece of hydrophobic nonwoven fabric joined to an outside surface of said side edge of the liquid impermeable layer.

9. A disposable absorbent article, comprising:
an absorbent core;
a liquid permeable topsheet positioned on top of said absorbent core;
and a backsheet assembly positioned beneath said absorbent core,
said backsheet assembly comprising a nonwoven fabric containing thermoplastic fibers and a thermoplastic film extruded onto said nonwoven fabric so as to include a central liquid impermeable layer in which said film is at its central portion secured to said nonwoven fabric, and opposite side marginal portions comprise nonwoven fabric;
said thermoplastic film including unsecured opposite side edges extending upwardly about respective opposite side edges of said absorbent core to form a pair of standing leg gathers,
each of said standing leg gathers further including an upper element each comprising hydrophobic nonwoven material, with each said upper element joined to a respective one of said side edges of said thermoplastic film, and elastic means operatively associated with an upper free edge portion of the respective upper element for elastically contracting each of the standing leg gathers.

* * * * *